United States Patent
Nishiyama et al.

(10) Patent No.: US 12,258,548 B2
(45) Date of Patent: Mar. 25, 2025

(54) METHOD FOR PRODUCING CULTURE VESSEL, AND CULTURE VESSEL

(71) Applicant: TOYO SEIKAN GROUP HOLDINGS, LTD., Tokyo (JP)

(72) Inventors: Takaharu Nishiyama, Kanagawa (JP); Satoshi Tanaka, Kanagawa (JP); Osamu Koseki, Kanagawa (JP); Takahiko Totani, Kanagawa (JP); Yosuke Matsuoka, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 883 days.

(21) Appl. No.: 17/411,780

(22) Filed: Aug. 25, 2021

(65) Prior Publication Data
US 2021/0380917 A1 Dec. 9, 2021

Related U.S. Application Data

(63) Continuation of application No. PCT/JP2020/006051, filed on Feb. 17, 2020.

(30) Foreign Application Priority Data

Feb. 27, 2019 (JP) .................................. 2019-034555

(51) Int. Cl.
*C12M 1/00* (2006.01)

(52) U.S. Cl.
CPC ............ *C12M 23/14* (2013.01); *C12M 23/26* (2013.01); *C12M 39/00* (2013.01)

(58) Field of Classification Search
CPC ........ C12M 23/14; C12M 23/26; C12M 23/20; C12M 23/12; C12M 39/00
See application file for complete search history.

(56) References Cited

U.S. PATENT DOCUMENTS

| 11,414,637 B2 | 8/2022 | Tanaka et al. |
| 2009/0181158 A1* | 7/2009 | Ikeya .................... C12M 23/20 427/2.13 |

(Continued)

FOREIGN PATENT DOCUMENTS

| CN | 108699500 A | 10/2018 |
| JP | H8-131153 A | 5/1996 |

(Continued)

OTHER PUBLICATIONS

Office Action issued in Chinese Patent Application No. 202080016462.6, dated Jul. 14, 2023, with English Translation of Substantial Part (20 pages).

(Continued)

*Primary Examiner* — Michael L Hobbs
(74) *Attorney, Agent, or Firm* — Nakanishi IP Associates, LLC

(57) ABSTRACT

In the production of a culture vessel in which a low cell-adhesive polymer as a coating agent is applied to a culture surface having a plurality of concave parts formed thereon, a use amount of the coating agent can be reduced. The low cell-adhesive polymer as the coating agent is applied to a surface of a culture base material in advance, and subsequently the culture base material is subjected to processing to form the culture vessel having the surface of the culture base material coated with the coating agent as the culture surface.

11 Claims, 4 Drawing Sheets

(MOLD WITH MICRO CONVEX PARTS)

(CULTURE SURFACE WITH MICRO CONCAVE PARTS)

(56) References Cited

U.S. PATENT DOCUMENTS

| | | | |
|---|---|---|---|
| 2011/0283758 A1* | 11/2011 | Carin | F26B 23/001 |
| | | | 432/9 |
| 2014/0326391 A1 | 11/2014 | Kuroda et al. | |
| 2017/0226456 A1 | 8/2017 | Kuroda et al. | |
| 2019/0031994 A1* | 1/2019 | Tanaka | C12M 23/04 |
| 2019/0161726 A1 | 5/2019 | Komazawa et al. | |
| 2020/0063083 A1 | 2/2020 | Miyatake et al. | |
| 2020/0148992 A1 | 5/2020 | Totani et al. | |
| 2022/0259538 A1 | 8/2022 | Totani et al. | |

FOREIGN PATENT DOCUMENTS

| | | | |
|---|---|---|---|
| JP | 2013-106531 A | 6/2013 | |
| WO | 2007/125894 A1 | 11/2007 | |
| WO | 2013/069490 A1 | 5/2013 | |
| WO | WO-2017170335 A1 * | 10/2017 | C12M 1/00 |
| WO | 2018/021566 A1 | 2/2018 | |
| WO | 2018/182044 A1 | 10/2018 | |
| WO | 2019/021748 A1 | 1/2019 | |

OTHER PUBLICATIONS

Extended European Search Report issued in European Patent Application No. 20762174.9, dated Oct. 17, 2022 (9 pages).
International Search Report issued in PCT/JP2020/006051 mailed on Apr. 7, 2020 with English Translation (5 pages).
Office Action issued in Japanese Patent Application No. 2019-034555 dated Aug. 18, 2021 (8 pages).

* cited by examiner

FIG1

| CONCENTRATION OF POLYMER SOLUTION (%) | USE AMOUNT OF POLYMER SOLUTION (mL) | TOTAL POLYMER WEIGHT (mg) | CELL ADHESION TO CONCAVE PARTS (YES/NO) |
|---|---|---|---|
| 2 | 1.5 | 30 | YES |
| 2 | 2 | 40 | NO |
| 2 | 3 | 60 | NO |

FIG2

| CONCENTRATION OF POLYMER SOLUTION (%) | TOTAL POLYMER WEIGHT (mg) | SURFACE DENSITY OF POLYMER (μg/cm²) | WELL DIAMETER (mm) | | | |
|---|---|---|---|---|---|---|
| | | | 0.5 | 2 | 4 | 7 |
| 4 | 20 | 100 | — | ▢ | — | — |
| 2 | 10 | 50 | — | ▢ | — | — |
| 0.5 | 2.5 | 15 | ▢ | ▢ | ▢ | ▢ |
| 0.15 | 0.83 | 5 | — | ▢ | — | — |
| 0.1 | 0.5 | 3 | — | ▢ | — | — |
| 0.067 | 0.33 | 2 | — | ▢ | — | — |
| — | 0 | NOT APPLIED | — | ▢ | — | — |

(MOLD WITH MICRO CONVEX PARTS)

(CULTURE SURFACE WITH MICRO CONCAVE PARTS)

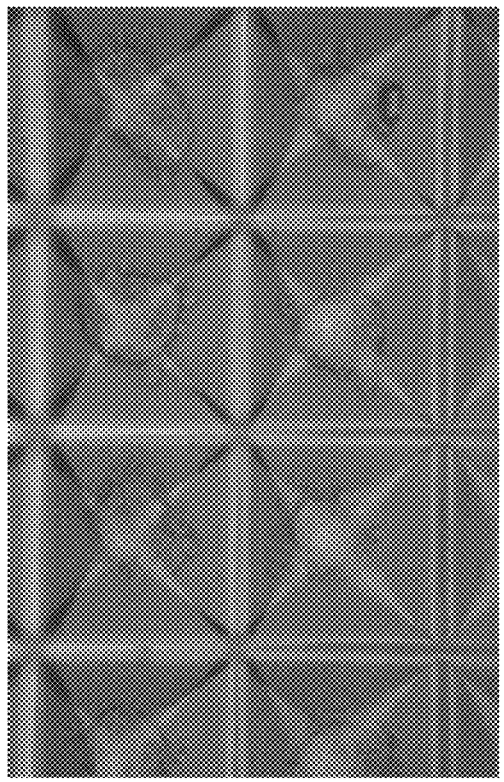
FIG4 (SPHERE FORMATION RESULT OF CULTURE VESSEL HAVING MICRO CONCAVE PARTS)

METHOD FOR PRODUCING CULTURE VESSEL, AND CULTURE VESSEL

TECHNICAL FIELD

The present invention relates to a cell culture technique, particularly, a method for producing a culture vessel subjected to a low cell-adhesion treatment.

BACKGROUND ART

In recent years, when stem cells such as iPS cells and ES cells are cultured, available methods include not only a method in which cells are cultured while being allowed to adhere to a culture vessel, but also a method in which cells are cultured in a three-dimensional state that more closely resembles the inside of a living body, where cells are allowed to adhere to and aggregate each other to form spheres (spheroids, aggregates) or organoids in a culture vessel.

In the cell culturing for forming the spheres, cells are cultured by using a culture vessel provided with a plurality of wells (concave parts) in a culture portion and allowing the cells to form the spheres in the concave parts.

In such a culture vessel for forming the spheres, for the purpose of preventing the cells from adhering to the surface of the culture portion (hereinafter, referred to as a "culture surface") of the culture vessel, the culture surface needs to be subjected to a low cell-adhesion treatment.

As the low cell-adhesion treatment, in general, a coating agent is applied to the culture surface, and a low cell-adhesion polymer is used as the coating agent.

Regarding this, when the low cell-adhesion polymer is applied to a culture vessel provided with relatively large size wells such as a 96-well plate, applying the polymer to each single well requires a large amount of time and work, and, thus, this has been a significant problem.

Further, as a method for uniformly applying the polymer to the wells, there is a method similar to a dip-coating method, in which the inside of the wells is entirely immersed into a polymer solution and then the solution is immediately removed. However, coating of the polymer by such a method requires a larger amount of the polymer solution than an amount of the polymer applied to the culture surface, causing a problem of high costs.

Further, when the low cell-adhesion polymer is applied to a culture vessel in which a plurality of concave parts extremely small in size are micro-processed in the culture portion, it is difficult to remove bubbles that enter the concave parts, causing a problem in that it is very difficult to uniformly apply the polymer to the culture surface. For example, in a case where the concave parts having openings of about from several tens of μm to 1 mm are formed on the culture surface, it is nearly impossible to remove the bubbles once trapped in the concave parts.

CITATION LIST

Patent Literature

Patent Literature 1: JP-A-8-131153
Patent Literature 2: JP-A-2013-106531

SUMMARY OF INVENTION

Technical Problem

As a method for applying a coating agent to the culture vessel provided with the wells, a cell culture vessel and a production method thereof described in Patent Literature 1 can be mentioned. In this method, a coating agent is injected in a plate provided with wells and then the coating agent is immediately sucked and discharged. After that, the plate is turned over and dried by air blowing to perform coating.

However, this method takes time and work and requires a large amount of the polymer solution, thus the problem of causing high costs cannot be solved by this method. Further, in this method, it is difficult to uniformly apply the coating agent to the culture vessel in which the concave parts extremely small in size are micro-processed.

Further, as a method for producing a culture vessel coated with a coating agent, a method for producing a cell culture vessel described in Patent Literature 2 can be mentioned. In this method, a base material to which a coating agent is applied in advance is integrated into a culture vessel by insert injection molding.

However, this method is not for applying a coating agent to the culture surface provided with a plurality of concave parts and thus cannot solve the above problem occurring when the coating agent is uniformly applied to the culture surface provided with a plurality of concave parts.

Regarding this, as a result of intensive studies, the present inventors have succeeded in reducing a concentration and an amount of a coating agent used for coating by applying a low cell-adhesion polymer as the coating agent to a surface of a culture base material in advance and then subjecting the culture base material to processing, thereby forming a culture vessel. Further, the present inventors have succeeded in obtaining a culture vessel that includes a culture surface provided with a plurality of concave parts extremely small in size, the culture surface being uniformly coated with a coating agent, thereby completing the present invention.

In view of the foregoing circumstances, an object of the present invention is to provide, in the production of a culture vessel in which a low cell-adhesion polymer as a coating agent is applied to a culture surface having a plurality of concave parts formed thereon, a method for producing the culture vessel capable of reducing a use amount of the coating agent, and the culture vessel.

Solution to Problem

In order to achieve the above object, a method for producing a culture vessel of the present invention includes: applying a low cell-adhesion polymer as a coating agent to a surface of a culture base material in advance; and subsequently processing the culture base material to form a culture vessel having the surface of the culture base material coated with the coating agent as a culture surface.

Further, in the method for producing the culture vessel of the present invention, it is preferable that the culture base material is in a film or a sheet shape, and the culture vessel is in a bag shape. It is also preferable that, in the processing, a plurality of concave parts are formed on the surface of the culture base material by concave-convex processing, and the processed surface is used as the culture surface of the culture vessel.

Further, in the method for producing the culture vessel of the present invention, it is preferable that, in the processing, the culture base material is formed in the bag shape and subsequently the concave-convex processing is performed by at least any of blow molding, vacuum molding, and pressure molding. It is also preferable that, in the processing, the concave-convex processing is performed by heat transfer and subsequently the culture base material is formed in the bag shape.

Further, a culture vessel of the present invention is provided with at least one port. A low cell-adhesion polymer is applied to a surface of a culture base material in a film or a sheet shape and subsequently the culture vessel is formed in a bag shape having the surface on which a plurality of concave parts are formed as a culture surface of the culture vessel. The low cell-adhesion polymer is not deposited to an inside of the port or a surface opposite to the culture surface in the culture vessel.

Advantageous Effects of Invention

According to the present invention, it becomes possible to provide, in the production of the culture vessel in which the low cell-adhesion polymer as the coating agent is applied to the culture surface having a plurality of concave parts formed thereon, the method for producing the culture vessel capable of reducing a use amount of the coating agent, and the culture vessel.

BRIEF DESCRIPTION OF DRAWINGS

FIG. 1 is a diagram showing a result of a test for confirming cell adhesion to concave parts in culture vessels obtained using a various amount of a polymer solution by a conventional method for producing a culture vessel.

FIG. 2 is a diagram showing a result of sphere formation using culture vessels in which concave parts are formed by vacuum pressure molding, produced by a method for producing a culture vessel according to an embodiment of the present invention.

FIG. 4 is a diagram showing a result of sphere formation using the culture vessel in which the concave parts are formed by heat transfer, produced by the method for producing the culture vessel according to the embodiment of the present invention.

DESCRIPTION OF EMBODIMENTS

Figure 3:
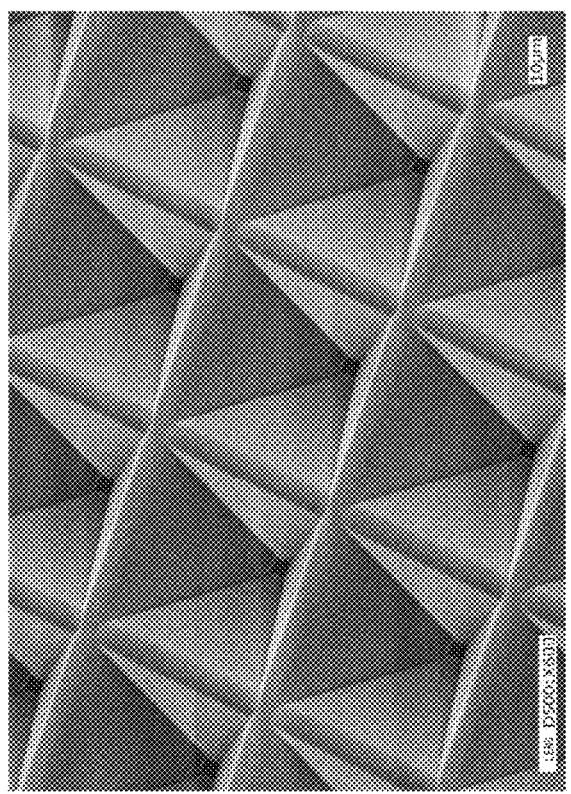
FIG. 3 is a diagram showing a microscopic image (700×) of a silicon mold having micro-convex parts used for performing concave-convex processing by heat transfer and a microscopic image (600×) of a culture surface having micro-concave parts obtained by using the silicon mold in the method for producing the culture vessel according to the embodiment of the present invention.
Figure 3:
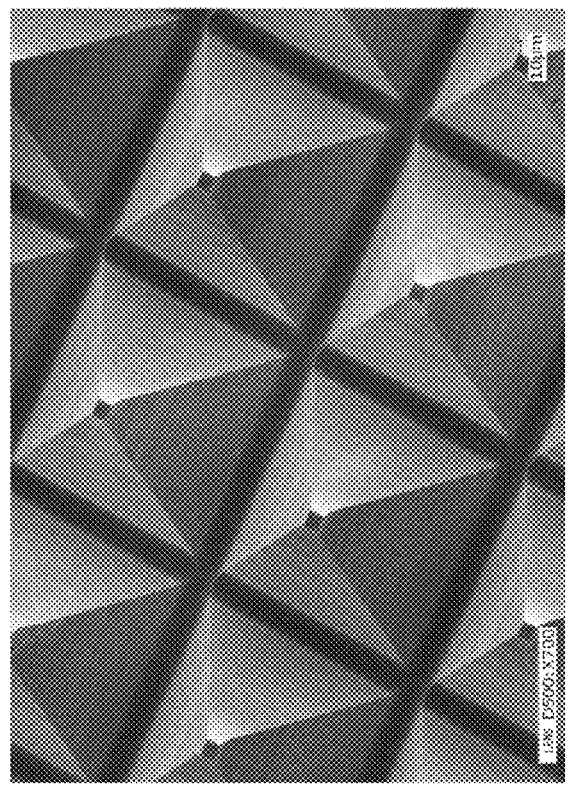

An embodiment of a method for producing a culture vessel and a culture vessel of the present invention will be described in detail below. However, the present invention is not limited to the following specific contents of the embodiment and Example.

The method for producing the culture vessel of the present embodiment is characterized in that a low cell-adhesion polymer as a coating agent is applied to a surface of a culture base material in advance and subsequently the culture base material is subjected to processing to form a culture vessel having the surface of the culture base material coated with the coating agent as a culture surface.

Application of the low cell-adhesion polymer to the surface of the culture base material can be suitably performed by using, for example, a bar coater or a gravure coater.

As the culture base material, a film or a sheet is preferably used.

As a material of the culture base material, an olefin resin such as polyethylene or polypropylene can be suitably used. Examples of other usable materials include polymethylpentene, a cyclic olefin polymer, a cyclic olefin copolymer, polyvinyl chloride, polyurethane, polymethyl methacrylate, polyester, polyamide, an ionomer, an ethylene-α-olefin copolymer, an ethylene-vinyl acetate copolymer, an ethylene-vinyl alcohol copolymer, an ethylene-acrylic acid copolymer, an ethylene-methacrylic acid copolymer, an ethylene-methyl methacrylate copolymer, polyacrylic acid, polymethacrylic acid, polymethyl acrylate, polymethyl methacrylate, polydimethylsiloxane, a fluoro resin, a silicone resin, a polybutadiene resin, and chlorinated polyethylene. Further, a thermoplastic elastomer such as an olefin based thermoplastic elastomer, a vinyl chloride-based thermoplastic elastomer, a styrene-based thermoplastic elastomer, a urethane-based thermoplastic elastomer, an ester-based thermoplastic elastomer, or a nylon-based thermoplastic elastomer can also be used. Further, a thermosetting elastomer such as urethane rubber, silicone rubber, or fluorine rubber and a thermosetting resin such as a phenol resin, an epoxy resin, a melamine resin, a urea resin, an unsaturated polyester resin, an alkyd resin, a urethane resin, or a thermosetting polyimide can also be used.

As the low cell-adhesion polymer applied to the surface of the culture base material, a phospholipid polymer, a polyvinyl alcohol derivative, a phospholipid-polymer complex, polyhydroxyethylmethacrylate, a polyvinyl alcohol, agarose, chitosan, polyethylene glycol, albumin, or the like can be used. Further, a combination thereof may also be used.

Further, the initial surface of the culture base material is preferably smooth in order to uniformly apply the low cell-adhesion polymer to the surface of the culture base material and perform the concave-convex processing on the applied surface.

The culture vessel to be formed is preferably a bag-shaped culture vessel formed of a soft packing material (a culture bag).

The culture bag can be formed by sticking peripheral parts of a lower surface film (a bottom portion-side film) and an upper surface film (a top plate-side film) together by heat sealing or the like.

In the culture bag, the surface of the culture base material coated with the low cell-adhesion polymer is formed as a culture surface. In this manner, when the spheres are formed or single cells are cultured using this culture bag, it becomes possible to prevent the spheres and the single cells from adhering to the culture surface.

The culture bag is provided with at least one port. This port is connected with a tube, and delivery of a medium such as injection of the medium into the culture bag and discharge of the medium from the culture bag is performed via the port by a liquid delivery means such as a pump disposed in the tube.

As a material of the port, for example, polyethylene, polypropylene, vinyl chloride, a polystyrene-based elastomer, or a thermoplastic resin such as FEP can be used.

In the method for producing the culture vessel of the present embodiment, first, the low cell-adhesion polymer is applied to the surface of the culture base material and subsequently the culture base material is subjected to processing.

As the processing of the culture base material, a plurality of concave parts are preferably formed on the surface (the upper surface of the bottom portion-side film) of the culture base material by the concave-convex processing. In this case, the surface on which the concave parts are formed is used as the culture surface in the culture vessel.

Further, in the processing of the culture base material, after the culture base material is formed in a bag shape, the concave-convex processing is performed preferably by at least any of blow molding, vacuum molding, and pressure molding. Further, the concave-convex processing is performed particularly preferably by vacuum pressure molding.

In the vacuum pressure molding, for example, the culture bag is placed in a mold in which openings of a size corresponding to a plurality of concave parts are formed, held by a jig for carrying out the vacuum pressure molding, and pressurized. A high-pressure air is blown in the culture bag, evacuation is performed from the outside of the mold, and the mold is heated to mold a plurality of concave parts in the culture bag.

Further, in the processing of the culture base material, it is also preferable that the concave-convex processing is performed by heat transfer and subsequently the culture base material is formed in a bag shape.

Specifically, a cushioning material is placed on a base material and a film or a sheet as the culture base material is placed on the cushioning material. Next, a mold in which convex parts corresponding to a plurality of concave parts are formed is placed on the culture base material and the culture base material is pressed from the top of the mold using a heating plate, so that the culture base material is heated while being pressurized to form a plurality of concave parts in the culture base material.

As this mold, a silicon mold, a metal mold such as nickel, or the like can be suitably used.

Further, in this operation, it is preferable that, for the purpose of facilitating peeling of the culture base material from the mold used for the heat transfer, a release agent is applied to the surface of this mold facing the culture base material and subsequently the concave-convex processing is performed.

As the release agent, a fluorine-based release agent or a silicon-based release agent can be suitably used.

Performing the processing of the culture base material in this manner can produce the culture bag having a large number of the micro concave parts on the culture surface. For example, the culture bag in which the diameter of the circle or the inscribed circle of the opening portions of the concave parts is from 1 µm or more to 10 mm or less can be suitably produced.

A plurality of concave parts formed on the culture surface of the bottom portion-side film of the culture bag can be formed in, for example, a conical shape such as a circular cone or a square cone, a hemispherical shape, or a round shape.

Further, it is also preferable that the concave parts formed on the culture surface of the bottom portion-side film have a shape in which at least apart of side walls is substantially vertically formed. Specifically, it is preferable that, in these concave parts, the length of the substantially vertical parts of the side walls in a vertical direction is longer than a half of the maximum diameter of objects to be cultured. Further, it is preferable that regions of the concave parts in which the side walls are substantially vertically formed are formed in, for example, a cylindrical shape, a quadrangular prism shape, or the like.

The concave parts of the culture bag having such a shape can prevent the objects to be cultured such as the spheres from jumping out of the concave parts and moving to other concave parts even when the medium is delivered in the culture bag from the port at a flow rate of 1 ml/min or more.

In a case where the objects to be cultured are the spheres, the depth of the concave parts is preferably from 50 to 500 µm. When the depth of the concave parts is more than 500 µm, it is sometimes difficult to sufficiently exchange the medium in the concave parts by delivering the medium to the culture bag, and it becomes more difficult to process the culture bag provided with the concave parts having a depth of more than 500 µm. Further, the above range is preferable because the size of the smaller spheres is about from 50 µm to 100 µm and the size of the larger spheres is about from 200 µm to 300 µm.

The shape of the bottom portions in the concave parts is not particularly limited. In a case where the objects to be cultured are the spheres, the shape is preferably a cone shape, a hemispherical shape, or a round shape for suitably forming the spheres by facilitating aggregation of single cells.

In a case where the objects to be cultured are single cells, the depth of the concave parts is preferably from 5 to 50 µm. This is because the size of the single cells is about from 6 µm to 15 µm, mostly about 10 µm.

The shape of the opening portions of the concave parts is not particularly limited. It can be a circular shape or a rectangular shape such as square. Further, the width of the opening portions of the concave parts can be appropriately set according to the size of the objects to be cultured.

For example, in a case where the objects to be cultured are the spheres, the lower limit of the diameter of the circle or the inscribed circle of the opening portions of the concave parts may be set to 60 µm or more, 70 µm or more, 80 µm or more, 90 µm or more, 100 µm or more, 110 µm or more, 120 µm or more, 150 µm or more, or the like. Further, the upper limit of the diameter of the circle or the inscribed circle of the opening portions of the concave parts may be set to 1 mm or less, 900 µm or less, 800 µm or less, 700 µm or less, 500 µm or less, or the like.

Further, in a case where the objects to be cultured are the single cells, the lower limit of the diameter of the circle or the inscribed circle of the opening portions of the concave parts may be set to 5 µm or more, 6 µm or more, 8 µm or more, or the like. Further, the upper limit of the diameter of the circle or the inscribed circle of the opening portions of the concave parts may be set 50 µm or less, 40 µm or less, 30 µm or less, or the like.

Further, a plurality of concave parts in the culture portion can be arranged in, for example, a staggered order, a latticed order, or the like.

Further, it is preferable that, in the processing of the culture base material, the low cell-adhesion polymer is applied only to the culture surface of the culture vessel. If the low cell-adhesion polymer is applied to a peripheral part of the culture surface or the like, this peripheral part is hardly heat sealed, making it difficult to form a bag shape.

Thus, it is preferable that a heat-sealable region where the low cell-adhesion polymer is not applied is provided to the culture base material by disposing a frame material (a masking material) on the culture base material before the low cell-adhesion polymer is applied to the culture base material.

Further, it is also preferable that, in the processing of the culture base material, the low cell-adhesion polymer is applied to the culture base material including the peripheral part of the culture surface of the bottom portion-side film of the culture vessel and subsequently the low cell-adhesion polymer applied to the peripheral part is subjected to an excimer treatment or ultraviolet-ray irradiation. This allows the peripheral part to be heat sealed. Further, it is also preferable that the low cell-adhesion polymer applied to the peripheral part is removed using a solvent.

Further, it is also preferable that the low cell-adhesion polymer is partially applied only to the culture surface of the culture vessel using a bar coater, a gravure coater, or the like.

Further, it is preferable that, in the processing of the culture base material, the surface of the culture base material is subjected to a hydrophilization treatment in advance and subsequently the low cell-adhesion polymer is applied to the treated surface. This can improve adhesion of the low cell-adhesion polymer to the surface of the culture base material.

According to such a method for producing the culture vessel of the present embodiment, the low cell-adhesion polymer is applied to the surface of the culture base material using a bar coater or the like in advance and subsequently a plurality of concave parts are formed on the culture surface by vacuum pressure molding, heat transfer, or the like, thereby making it possible to obtain the culture vessel having such a culture surface.

This can significantly reduce the amount of the low cell-adhesion polymer required for coating as described in Example below.

Further, in particular, even when the culture bag in which the concave parts extremely small in size are micro-processed is produced, it becomes possible to obtain the culture bag in which the low cell-adhesion polymer is uniformly applied to the culture surface.

Note that such a method for producing the culture vessel of the present embodiment can also be applied to a case where a material other than the low cell-adhesion polymer, such as, for example, a coating agent made of proteins resistant to dryness, is used as the coating agent.

Further, the culture vessel produced by the present embodiment is preferably configured such that top plate projections are provided on the top plate-side film inside the culture vessel, the width of the top plate projections is made smaller than the width of the opening portions of the concave parts formed on the bottom portion-side film, and the height of the top plate projections is made smaller than the minimum diameter of the objects to be cultured, so that, when the top plate projections come into contact with parts of the upper end surface of the culture portion, gaps are formed between the upper end surface and the lower surface of the top plate-side film.

In the culture vessel of the present embodiment having such a configuration, when the top plate projections come into contact with the parts of the upper end surface, the gaps smaller than the size of the objects to be cultured can be formed between the upper end surface and the top plate portion. This allows a liquid object such as the medium to pass through the gaps while preventing the relocation of the objects to be cultured such as the spheres.

The culture vessel of the present embodiment provided with at least one port is characterized in that the low cell-adhesion polymer is applied to the surface of the culture base material formed in a film or a sheet shape and subsequently the culture vessel is formed in a bag shape having the surface on which a plurality of concave parts are formed as a culture surface of the culture vessel, and the low cell-adhesion polymer is not deposited to an inside of the port or a surface opposite to the culture surface in the culture vessel.

That is, as is the case with a conventional method, when the low cell-adhesion polymer is injected into a culture vessel formed in a bag shape and immediately sucked and discharged, and then the culture vessel is turned over and dried, the low cell-adhesion polymer is deposited to the inside of the port and the surface opposite to the culture surface (the lower surface of the top plate-side film inside the culture vessel) in the obtained culture vessel, causing a problem of requiring an excessive amount of the low cell-adhesion polymer.

On the other hand, the culture vessel of the present embodiment is obtained in a bag shape such that the low cell-adhesion polymer is applied to the surface of the culture base material and subsequently a plurality of concave parts are formed on the applied surface by the concave-convex processing, the resulting surface being used as the culture surface. Thus, the culture vessel is characterized in that the low cell-adhesion polymer is not deposited to the inside of the port or the surface opposite to the culture surface.

This makes it possible to solve the problem of requiring an excessive amount of the low cell-adhesion polymer in the conventional method.

Further, in the culture vessel of the present embodiment, the surface density of the low cell-adhesion polymer applied to the culture surface is preferably from 100 $\mu g/cm^2$ to 1 $\mu g/cm^2$.

This is because, as described in Example below, the culture vessel of the present embodiment can be obtained by applying the low cell-adhesion polymer at a surface density of as small as 100 $\mu g/cm^2$, 50 $\mu g/cm^2$, 15 $\mu g/cm^2$, 5 $\mu g/cm^2$, 3 $\mu g/cm^2$, or 2 $\mu g/cm^2$. Further, this is because, performing the concave-convex processing for forming the concave parts having a hemispherical shape on the culture surface decreases the surface density of the low cell-adhesion polymer by half.

EXAMPLES

Hereinafter, a description is given of tests performed for confirming effects of the method for producing the culture vessel and the culture vessel of the embodiment of the present invention.

(Test 1)

First, as a comparative example, a test was performed for confirming an amount of a low cell-adhesion polymer required in a conventional method in which a plurality of concave parts are formed on a culture surface of a culture bag and subsequently the low cell-adhesion polymer is applied to the culture surface.

Specifically, a plurality of films having a rectangular shape with a long side of 12 cm and a short side of 7.5 cm were produced using LLDPE (linear low-density polyethylene). Then, half of the films were used as bottom portion-side films and the other half were used as top plate-side films.

Next, the bottom portion-side film and the top plate-side film were overlayed and peripheral parts thereof were stuck together by heat sealing to forma culture bag. In this operation, a port was inserted in one side of the culture bag and stuck together to produce a culture bag provided with one port.

Next, the culture bag was held by a jig manufactured by our company including a mold for forming a plurality of concave parts in which the diameter of opening portions is 2 mm and pressurized. A high-pressure air was blown in the culture bag while evacuation was performed from the outside of the mold, and the lower mold was heated to 80° C. to mold a plurality of concave parts having a hemispherical shape in the culture bag by vacuum pressure molding.

In this manner, three culture bags in which a plurality of concave parts were densely arranged in a staggered order on the entire surface of the culture surface and the culture portion had an area of 60 $cm^2$ were produced.

Next, the obtained culture bag was filled with an MPC polymer solution as a low cell-adhesion polymer with a concentration of 2%, and then the solution was immediately discharged. The culture bag was arranged upside down and left to stand still for drying.

In this operation, three different amounts of the MPC polymer solution, 1.5 mL, 2 mL, and 3 mL, were filled in the culture bags for producing the three culture bags.

Then, each culture bag was filled with StemFit AK02N (item number: RCAK02N, AJINOMOTO Co., Inc.) as a medium and inoculated with iPS cells (the strain 1231A3). After 24 hours, it was confirmed whether the cells were adhered to the surface of the concave parts. The result is shown in FIG. 1.

In this test, it can be assumed that the cells are not adhered to the concave parts if the MPC polymer is appropriately applied to the concave parts of the culture bag, while the cells are adhered to the concave parts if the MPC polymer is not appropriately applied to the concave parts of the culture bag.

As shown in FIG. 1, when the amount of the MPC polymer solution filled in the culture bag was 1.5 mL, the cells were adhered to the concave parts. In this condition, the total amount of the MPC polymer was 30 mg.

On the other hand, when the amounts of the MPC polymer solution filled in the culture bag were 2 mL and 3 mL, the cells were not adhered to the concave parts. In this condition, the total amounts of the MPC polymer were 40 mg and 60 mg, respectively.

That is, it was found that, in order to appropriately apply the low cell-adhesion polymer to the culture bag in which a plurality of concave parts were provided and the culture portion had an area of 60 cm$^2$, as described above, at least 2 mL of the solution was required in the conventional method.

(Test 2)

Next, the test was performed for a case where the culture bag in which the concave parts were formed by vacuum pressure molding was produced according to the method for producing the culture vessel of the present embodiment.

Specifically, a plurality of films having a rectangular shape with a long side of 12 cm and a short side of 7.5 cm were produced using LLDPE (linear low-density polyethylene). Then, half of the films were used as the bottom portion-side films and the other half were used as the top plate-side films.

Then, the MPC polymer as the low cell-adhesion polymer was applied to a region of one surface of the bottom portion-side film except for peripheral parts by using a bar coater (ROD. No. 3, YASUDA SEIKI SEISAKUSHO, Ltd.), and this region was used as the culture surface. The solution amount used for coating is 0.5 mL and the area of the culture surface coated with the low cell-adhesion polymer is 60 cm$^2$.

The solution amount of 0.5 mL used for this coating was the minimum amount of the solution required for coating the coating area of 60 cm$^2$ by using a bar coater, and it was difficult to coat the coating area of 60 cm$^2$ if the solution amount was less than this amount.

In this test, six different concentrations of the MPC polymer, 4%, 2%, 0.5%, 0.15%, 0.1% and 0.067%, were prepared to produce four bottom portion-side films coated with the MPC polymer with a concentration of 0.5% and one each of the bottom portion-side films coated with the MPC polymer with other concentrations, and these eight films were used as Example.

The total amount of the MPC polymer used for producing the bottom portion-side films coated with the MPC polymer with concentrations of 4%, 2%, 0.5%, 0.15%, 0.1%, and 0.067% is 20 mg, 10 mg, 2.5 mg, 0.83 mg, 0.5 mg, and 0.33 mg, respectively.

Further, the MPC polymer was not applied to one of the bottom portion-side films, and this film was used as Comparative example.

Further, the surface density of the MPC polymer applied to the culture surface of the bottom portion-side films used in Example was measured by using Fourier transformation infrared spectrophotometer (item number: FTS7000, Varian, Inc.).

Aa a result, the surface density of the MPC polymer of the bottom portion-side films coated with the MPC polymer with concentrations of 4%, 2%, 0.5%, 0.15%, 0.1%, and 0.067% was 100 μg/cm$^2$, 50 μg/cm$^2$, 15 μg/cm$^2$, 5 μg/cm$^2$, 3 μg/cm$^2$, and 2 μg/cm$^2$, respectively.

Next, the top plate-side film was overlayed on the bottom portion-side film such that the culture surface of the bottom portion-side film coated with the MPC polymer was arranged inside, and peripheral parts thereof were stuck together by heat sealing to form a culture bag. Further, in this operation, a port was inserted in one side of the culture bag and stuck together.

Then, the culture bag was held by a jig manufactured by our company including a mold for forming concave parts of various prescribed sizes and pressurized. A high-pressure air was blown in the culture bag while evacuation was performed from the outside of the mold, and the lower mold was heated to 80° C. to mold a plurality of concave parts having a hemispherical shape in the culture bag by vacuum pressure molding.

In this manner, one culture bag in which a plurality of concave parts with the diameter of the opening portions of 0.5 mm were densely arranged in a staggered order on the entire surface of the culture surface, seven culture bags in which a plurality of concave parts with the diameter of the opening portions of 2 mm were arranged in the same manner, one culture bag in which a plurality of concave parts with the diameter of the opening portions of 4 mm were arranged in the same manner, and one culture bag in which a plurality of concave parts with the diameter of the opening portions of 7 mm were arranged in the same manner were produced.

Among the culture bags provided with the plurality of concave parts with the diameter of the opening portions of 2 mm, five culture bags were applied with the MPC polymer with five different concentrations in Example, and one culture bag was not applied with the MPC polymer and used as Comparative example.

Among the culture bags provided with the plurality of concave parts with the diameter of the opening portions of 0.5 mm, 4 mm, and 7 mm, one each culture bag was applied with the MPC polymer with a concentration of 0.5% in Example.

The ports of the culture bags thus obtained were connected with tubes and the medium was delivered to the culture bags via the tubes.

Then, the spheres were formed in these culture bags using the iPS cells (the strain 1231A3).

Specifically, the number of inoculated cells was about 3.0×10$^6$ cells. Further, StemFit AK02N (item number: RCAK02N, AJINOMOTO Co., Inc.) was used as the medium. The above medium containing 10 mM Y-27632 (Wako Pure Chemical Industries, Ltd.) was injected into the culture bags and cell suspensions containing the above iPS cells were injected. The culture bags were left to stand still for overnight. The result is shown in FIG. 2.

As shown in FIG. 2, the spheres could be appropriately formed in any of the culture bags obtained according to the method for producing the culture vessel of the present embodiment.

On the other hand, the spheres could not be formed in the culture bag in which the MPC polymer was not applied to the culture surface.

As described above, in the method for producing the culture vessel of the present embodiment, the solution amount used for coating was 0.5 mL, and the MPC polymer could be applied to the culture surface with an amount less than 2 mL which was the minimum amount necessary in Comparative example in Test 1.

Further, in Comparative example in Test 1, at least 40 mg was required as the total polymer amount. In contrast, according to the method for producing the culture vessel of the present embodiment, in a case where the MPC polymer solution was used with a concentration of 2%, the same concentration as in Comparative example in Test 1, the total used polymer amount was 10 mg, demonstrating that the coating could be performed with 25% of the total polymer amount in Comparative example.

Further, in a case of the MPC polymer solution with a concentration of 0.5%, the total used polymer amount was 2.5 mg, demonstrating that the coating could be performed with 6.25% of the total polymer amount in Comparative example. Further, in a case of the MPC polymer solution with a concentration of 0.15%, the total used polymer amount was 0.83 mg, demonstrating that the coating could be performed with 2.075% of the total polymer amount in Comparative example. Further, in a case of the MPC polymer solution with a concentration of 0.1%, the total used polymer amount was 0.5 mg, demonstrating that the coating could be performed with 1.25% of the total polymer amount in Comparative example. Further, in a case of the MPC polymer solution with a concentration of 0.067%, the total used polymer amount was 0.33 mg, demonstrating that the coating could be performed with 0.825% of the total polymer amount in Comparative example.

As described above, according to the method for producing the culture vessel and the culture vessel of the present embodiment, it was found that the use amount of the polymer could be significantly reduced.

Note that, in the method for producing the culture vessel of the present embodiment, the MPC polymer was applied to the smooth bottom portion-side film and then the concave parts having a hemispherical shape were formed on the culture surface. Thus, the surface area of the concave parts after the processing was increased to twice of its original surface area. That is, in a case where the surface density of the MPC polymer on the culture surface is 2 $\mu g/cm^2$, the surface density of the MPC polymer on the culture surface after the processing is about 1 $\mu g/cm^2$, representing the minimum coating amount in Example shown in FIG. 2.

(Test 3)

Next, the test was performed for a case where the culture bag in which the concave parts were formed by heat transfer was produced according to the method for producing the culture vessel of the present embodiment.

Specifically, a plurality of films having a rectangular shape with a long side of 12 cm and a short side of 7.5 cm were produced using LLDPE (linear low-density polyethylene). Then, half of the films were used as the bottom portion-side films and the other half were used as the top plate-side films.

Then, the MPC polymer as the low cell-adhesion polymer was applied to a region of one surface of the bottom portion-side film except for peripheral parts by using a bar coater (ROD. No. 3, YASUDA SEIKI SEISAKUSHO, Ltd.), and this region was used as the culture surface. The solution amount used for coating is 0.5 mL and the area of the culture surface coated with the low cell-adhesion polymer is 60 $cm^2$.

In this test, the concentration of the MPC polymer was 0.5%, and one bottom portion-side film coated with the MPC polymer was produced. The total amount of the MPC polymer used for producing the bottom portion-side film is 2.5 mg.

Further, the surface density of the MPC polymer applied to the culture surface of the bottom portion-side film used in Example was measured by using Fourier transformation infrared spectrophotometer (item number: FTS7000, Varian, Inc.). Aa a result, the surface density of the MPC polymer of the bottom portion-side films was 15 $\mu g/cm^2$.

Next, this bottom portion-side film was subjected to heat transfer to perform the concave-convex processing.

Specifically, a cushioning material was placed on a base material and the bottom portion-side film described above was placed on the cushioning material.

Next, a silicon mold was placed on the bottom portion-side film and the culture base material was pressed from the top of the mold using a heating plate, so that the culture base material was heated while being pressurized to perform the concave-convex processing on the culture surface of the bottom portion-side film.

In this operation, the heating temperature of the silicon mold was 120° C. and the pressure was 0.4 MPa. Further, the pressurizing time was 8 seconds.

Further, in this operation, the concave-convex processing was performed after a release agent was applied to the silicon mold. As the release agent, a fluorine-based release agent (Fluoro Surf FG-5084, manufactured by Fluoro Technology) was used.

As shown in a left image in FIG. 3, the silicon mold in which micro-convex parts having a quadrangular pyramid shape were densely arranged in a lattice order was used. One side of opening portions of the silicon mold is 160 $\mu m$ and the height of the convex parts is 150 $\mu m$.

Further, as shown in a right image in FIG. 3, the culture surface of the bottom portion-side film produced by using this mold had micro concave parts with a quadrangular pyramid shape densely arranged in a lattice order on the entire culture surface.

Next, the top plate-side film was overlayed on the bottom portion-side film such that the culture surface of the bottom portion-side film to which the MPC polymer was applied and on which a plurality of concave parts were formed was arranged inside, and peripheral parts thereof were stuck together by heat sealing to form a culture bag. Further, in this operation, a port was inserted in one side of the culture bag and stuck together.

The port of the culture bag thus obtained was connected with a tube and the medium was delivered to the culture bag via the tube.

Then, the spheres were formed by this culture bag using the iPS cells (the strain 1231A3).

Specifically, the cells were inoculated into the concave parts at 200 single cells per concave part. Further, StemFit AK02N (item number: RCAK02N, AJINOMOTO Co., Inc.) was used as the medium. The above medium containing 10 mM Y-27632 (Wako Pure Chemical Industries, Ltd.) was injected into the culture bag and a cell suspension containing the above iPS cells was injected. The culture bag was left to standstill for overnight. The result is shown in FIG. 4.

As shown in FIG. 4, the sphere with a size of about 80 μm was properly formed in each of the concave parts.

Further, in the Test 3, the MPC polymer solution with a concentration of 0.5% is used, and this total polymer amount is 2.5 mg.

That is, the coating could be sufficiently performed with 6.25% of the minimum total polymer amount of 40 mg in Comparative example in Test 1. Thus, the present test also demonstrated that the use amount of the polymer could be significantly reduced.

As described above, according to the method for producing the culture vessel and the culture vessel according to the present embodiment of the present invention, it was found that, for obtaining the culture vessel in which the low cell-adhesion polymer was applied to the culture surface having a plurality of concave parts formed thereon, the use amount of the coating agent could be significantly reduced.

The present invention is not limited to the above embodiment and Example, and it is needless to say that various modifications can be made within the scope of the present invention.

As an example of appropriate modifications, the size of the culture bag to be produced is not limited to the size in Example, and the size can be adjusted to a size capable of forming, for example, 500,000 to 1 million spheres.

INDUSTRIAL APPLICABILITY

The present invention can be suitably used in a case where the spheres with a uniform size arranged at equal intervals are efficiently mass produced, and the like.

The documents described in this specification and the Japanese application specification claiming priority under the Paris Convention are incorporated herein by reference in its entirety.

The invention claimed is:

1. A method for producing a culture vessel, comprising:
applying a low cell-adhesion polymer as a coating agent to a surface of a culture base material in advance; and
subsequently processing the culture base material to form a culture vessel having the surface of the culture base material coated with the coating agent as a culture surface, wherein,
in the processing, a plurality of concave parts are formed on the surface of the culture base material by concave-convex processing, and the processed surface is used as the culture surface of the culture vessel.

2. The method for producing the culture vessel according to claim 1, wherein
the culture base material is in a film or a sheet shape, and the culture vessel is in a bag shape.

3. The method for producing the culture vessel according to claim 1, wherein
in the processing, the culture base material is formed in the bag shape, and subsequently the concave-convex processing is performed by at least any of blow molding, vacuum molding, and pressure molding.

4. The method for producing the culture vessel according to claim 1, wherein
in the processing, the concave-convex processing is performed by heat transfer, and subsequently the culture base material is formed in the bag shape.

5. The method for producing the culture vessel according to claim 4, comprising
applying a release agent to a mold used in the heat transfer; and
subsequently performing the concave-convex processing.

6. The method for producing the culture vessel according to claim 1, wherein
a diameter of a circle or an inscribed circle of opening portions of the concave parts is from 1 mm or more to 10 mm or less.

7. The method for producing the culture vessel according to claim 1, comprising
applying the coating agent only to the culture surface of the culture vessel.

8. The method for producing the culture vessel according to claim 1, comprising
disposing a frame material on the culture base material; and
subsequently applying the coating agent to the culture base material to provide a heat-sealable region in the culture base material where the coating material is not applied.

9. The method for producing the culture vessel according to claim 1, comprising
performing a hydrophilization treatment on the surface of the culture base material in advance; and
subsequently applying the coating material to the treated surface.

10. The method for producing the culture vessel according to claim 1, wherein
a surface density of the low cell-adhesion polymer applied to the surface is from 100 mg/cm$^2$ to 1 mg/cm$^2$.

11. The method for producing the culture vessel according to claim 1, wherein the low cell-adhesion polymer applied to the surface of the culture base material is selected from a phospholipid polymer, a polyvinyl alcohol derivative, a phospholipid-polymer complex, polyhydroxyethylmethacrylate, a polyvinyl alcohol, agarose, chitosan, polyethylene glycol, and albumin.

* * * * *